（12) United States Patent
Baxa et al.

(10) Patent No.: US 6,338,200 B1
(45) Date of Patent: Jan. 15, 2002

(54) SYRINGE DOSE IDENTIFICATION SYSTEM

(75) Inventors: Ronald Dale Baxa, Littleton; Brian E. Baldwin, Aurora, both of CO (US)

(73) Assignee: Baxa Corporation, Englewood, CO (US)

( * ) Notice: Subject to any disclaimer, the term of this patent is extended or adjusted under 35 U.S.C. 154(b) by 0 days.

(21) Appl. No.: 09/415,366

(22) Filed: Oct. 8, 1999

(51) Int. Cl.$^7$ .............. G01F 13/00; G06G 1/00
(52) U.S. Cl. .............. 33/494; 33/1 V; 33/679.1; 222/386
(58) Field of Search ............. 33/1 F, 1 V, 483, 33/484, 485, 494, 755, 759, 760, 501, 511, 512, 522, 679.1; 222/386, 206

(56) References Cited

U.S. PATENT DOCUMENTS

| | | | |
|---|---|---|---|
| 461,106 A | * | 10/1891 | Oberly ............. 33/494 |
| 1,964,425 A | * | 6/1934 | Bowman ............. 33/485 |
| 3,568,923 A | * | 3/1971 | Chapman ............. 33/485 |
| 4,056,096 A | | 11/1977 | Collica et al. ......... 128/1.1 |
| 4,091,812 A | | 5/1978 | Helixon et al. |
| 4,303,071 A | | 12/1981 | Smith |
| 4,317,448 A | | 3/1982 | Smith |
| 4,447,232 A | | 5/1984 | Sealfon et al. |
| 4,464,941 A | | 8/1984 | Herold et al. |
| 4,475,905 A | | 10/1984 | Himmelstrup ......... 604/208 |
| 4,493,348 A | | 1/1985 | Lemmons |
| 4,495,709 A | * | 1/1985 | Mainenti ............. 33/484 |
| 4,521,237 A | | 6/1985 | Logothetis |
| 4,557,728 A | | 12/1985 | Sealfon et al. |
| 4,713,888 A | | 12/1987 | Broselow |
| 4,738,663 A | | 4/1988 | Bogan |
| 4,747,839 A | | 5/1988 | Tarello et al. |
| 4,781,689 A | | 11/1988 | Sealfon et al. |
| 4,823,469 A | | 4/1989 | Broselow |
| 5,010,656 A | | 4/1991 | Broselow |
| 5,186,180 A | * | 2/1993 | Bellas ............. 33/512 |
| 5,195,993 A | | 3/1993 | Gianakos |
| 5,279,582 A | | 1/1994 | Davison et al. |
| 5,336,189 A | | 8/1994 | Sealfon |
| 5,487,750 A | | 1/1996 | Burchett et al. |
| 5,498,243 A | | 3/1996 | Vallelunga et al. |
| 5,823,998 A | | 10/1998 | Yamagata |

* cited by examiner

Primary Examiner—Christopher W. Fulton
(74) Attorney, Agent, or Firm—Hogan & Hartson, LLP

(57) ABSTRACT

The present invention may be used to dispense a dose of medication to a patient from a syringe having a barrel adapted for receiving the medication and a plunger adapted for drawing the medication into the barrel and dispensing the medication from the syringe. The medication dose is based on a measurement or value associated with a patient that corresponds to a coded range. The present invention includes a sleeve mounted on the barrel of the syringe. The sleeve contains indicia corresponding to a plurality of the coded ranges. In one embodiment, the indicia include a plurality of colored marks corresponding to a plurality of the coded ranges indicative of different doses of the medication. In another embodiment, the indicia is a color of a tinted, substantially transparent sleeve.

24 Claims, 12 Drawing Sheets

SYRINGE DOSE IDENTIFICATION SYSTEM

BACKGROUND OF THE INVENTION

1. Field of the Invention

The present invention generally relates to medicine dosages, and more particularly, to techniques for labeling syringes to assist in providing appropriate dosages of medicine during emergencies.

2. Description of the Related Art

Physicians conventionally base drug dosages on a patient's weight. When the physician does not know the weight, the physician bases the dose on an estimate, or best guess, of the weight. The possibility that the doctor will misjudge weight increases during emergency situations. Misjudging the patient's weight leads to giving the incorrect dose of medicine. Therefore, it is desirable to have a more objective and easily obtainable measurement of a patient to be used to determine the correct dose of medicine.

Dr. James B. Broselow has invented a method of utilizing an objective and easily obtainable measurement to determine drug dose. As described in U.S. Pat. No. 4,713,888 to Broselow entitled MEASURING TAPE FOR DIRECTLY DETERMINING PHYSICAL TREATMENT AND PHYSIOLOGICAL VALUES, U.S. Pat. No. 4,823,469 to Broselow entitled MEASURING TAPE FOR DIRECTLY DETERMINING PHYSICAL TREATMENT AND PHYSIOLOGICAL VALUES AND PROCEDURES, and U.S. Pat No. 5,010,656 to Broselow entitled THERAPEUTIC APPARATUS, the disclosures of which are incorporated herein by reference, Dr. Broselow has developed a technique in which drug dosages are correlated to a patient's length, which is readily measurable. It is recommended that the Broselow patents be read in their entirety to fully appreciate the method and teachings disclosed therein.

More particularly, and referring now to FIGS. 1–3, a drug dose may be determined by reference to a patient's length in the following way. Tape 10 is used by a physician to measure a patient's length. Tape 10 includes an enclosure 12 into which tape 10 can be retracted and a pull tab 14. Rather then containing length measurements in inches, centimeters, or the like, tape 10 is segmented into color range indicia 2, 4, 6, 8, etc. For purposes of example only, color range 2 may be red, color range 4 green, color range 6 yellow, and color range 8 blue. It can readily be appreciated, however, that other color or marking schemes may be used. Moreover, tape 10 may contain length measurements in inches, centimeters, or the like and also include indicia 2, 4, 6, 8, etc.

FIG. 2 illustrates a cup 20 like that disclosed by Dr. Broselow in U.S. Pat. No. 5,010,656 (FIG. 7 and related description therein), from which medicine may be dispensed. Cup 20 is marked with a series of lines 22, 24, 26, 28, etc. In this example, lines 22, 24, 26, and 28 of cup 20 correspond to color range indicia 2, 4, 6, and 8 of tape 10, with indicia 22 red, indicia 24 green, indicia 26 yellow, and indicia 28 blue.

Referring now to FIG. 3, an operator 32 (for example, a nurse, physician or technician) places pull tab 14 of tape 10 at the heel 36 of a patient 34. Operator 32 moves enclosure 12 along patient 34 until enclosure 12 reaches a crown 38 of patient 34. A corresponding color range indicia on tape 10 (for example, range 4 green) which aligns with the crown 38 of patient 34, is read and noted. Operator 32 then dispenses medicine to patient 34 by filling cup 20 with medicine until the top surface of the medicine is aligned with the line on cup 20 which corresponds to the noted color range on tape 10. In this example, operator 32 fills cup 20 to green line 24, and the patient then drinks the medicine dose from cup 20. Similarly, red range indicia 2 on tape 10 matches red line 22 on cup 20, etc. In this way, the length of patient 34 is directly correlated to a volumetric dose of a medicine dispensed from a cup. As is more fully described in the Broselow patents, correlations can be made to other apparatus (e.g., tube lengths) and device settings.

It must be noted, however, that while providing indicia on cup 20 corresponding to indicia on tape 10 improves the dispensation of medicine, it greatly complicates the manufacturing process of molding cup 20. Conventional imprinting techniques may require multiple runs of the cups through the printing machines. Furthermore, inventories having different dispensers imprinted for different types of medicine may need to be maintained at a prohibitively high cost.

Of course medicines are dispensed to patients from containers other than cup 20 as described above. In particular, syringes are widely used to dispense fluids to patients. Intravenous, hypodermic and oral syringes are variously used to dispense medications and other fluids to patients. While syringes for different purposes often have different features and attachments, they typically contain a cylindrical barrel which receives and contains the medication to be dispensed and a plunger slidably mounted in the barrel. The plunger is withdrawn away from the forward end of the barrel to draw medicine into the barrel and pushed towards the forward end of the barrel to dispense medicine from the barrel out of the tip of the syringe.

Syringes often have volumetric markings on the barrel (e.g. ounce or cubic centimeter (cc)), with such markings typically imprinted in a single color, often black, during a single pass in the manufacturing process. It can readily be appreciated that imprinting even a single color on conventional syringes during the manufacturing process is naturally complicated by the 3-dimensional nature of the syringe, the cylindrical shape of the barrel, and volumetric variations in barrel capacity. When multiple imprinting is contemplated, consistent registration of lines on a syringe may be difficult to monitor and may require multiple quality control checks to ensure accuracy of the volumes indicated by all of the different marks. Accordingly, it is postulated that implementation of the color/dose correlation system disclosed in the Broselow patents with syringes by multiple color imprinting techniques may well be discouraged by prohibitively high manufacturing costs.

OBJECTS OF THE INVENTION

It is a principal object of the present invention to provide a means of placing a removable and reusable drug dose marking on a specific size standard syringe filled or to be filled with a known medication.

It is a further object of the present invention to provide such a removable and reusable drug dose marking means so that a specific patient regimen for a drug can be followed without requiring customized syringes for the patient.

It is a further object of the present invention to provide such a removable and reusable drug dose marking means without the necessity for customizing syringes for different doses and strengths of different medications at the time the syringes are produced.

SUMMARY OF THE INVENTION

The present invention includes a removable and reusable sleeve adapted for mounting on the barrel of a syringe from which a dose of medication is to be dispensed to a patient. The syringe includes a barrel adapted for receiving the medication and a plunger adapted for drawing the medication into the barrel and dispensing the medication therefrom. The medication dose is based on a measured length or other value of the patient that corresponds to one of a plurality of coded ranges. The sleeve of the present invention contains indicia corresponding to a plurality of the coded ranges. In the preferred embodiment of the present invention, the indicia include a plurality of colored marks corresponding to a plurality of the coded ranges indicative of different doses of the medication. In another embodiment of the present invention, the sleeve contains a single black or colored mark. In yet another embodiment, the sleeve also contains alignment or positioning indicia. In still yet another embodiment, the sleeve of the present invention is color tinted to correspond to a coded range.

BRIEF DESCRIPTION OF THE INVENTION

DETAILED DESCRIPTION OF THE PREFERRED EMBODIMENTS

Figure 4:
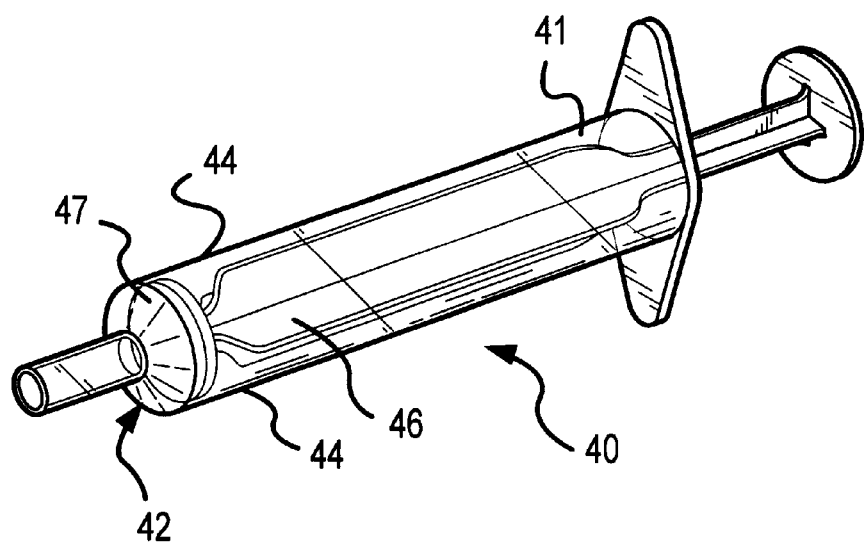
FIG. 4 (prior art) is a perspective view of a conventional syringe.
Figure 6:
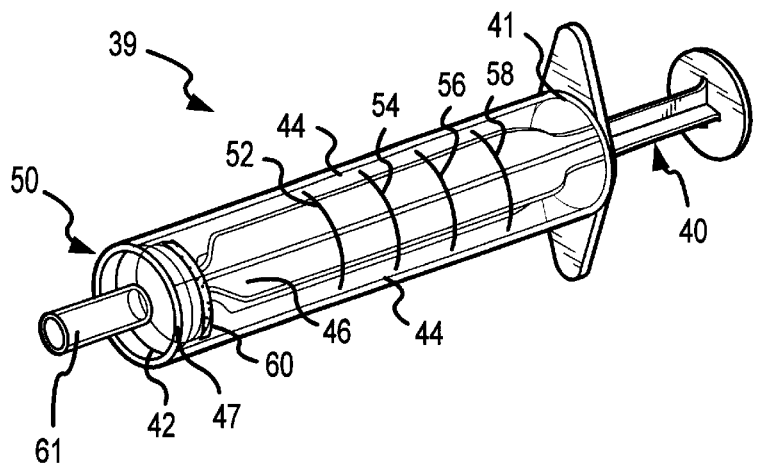
FIG. 6 is a perspective view of the syringe shown in FIG. 4 fitted with the sleeve shown in FIG. 5, prior to filling the syringe.
Figure 7:
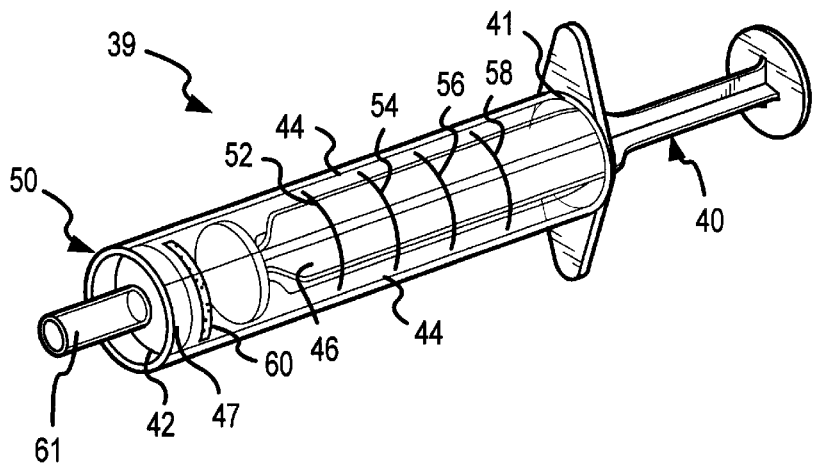
FIG. 7 is a perspective view of the syringe and sleeve shown in FIG. 6, after partially filling the syringe.
Figure 8:
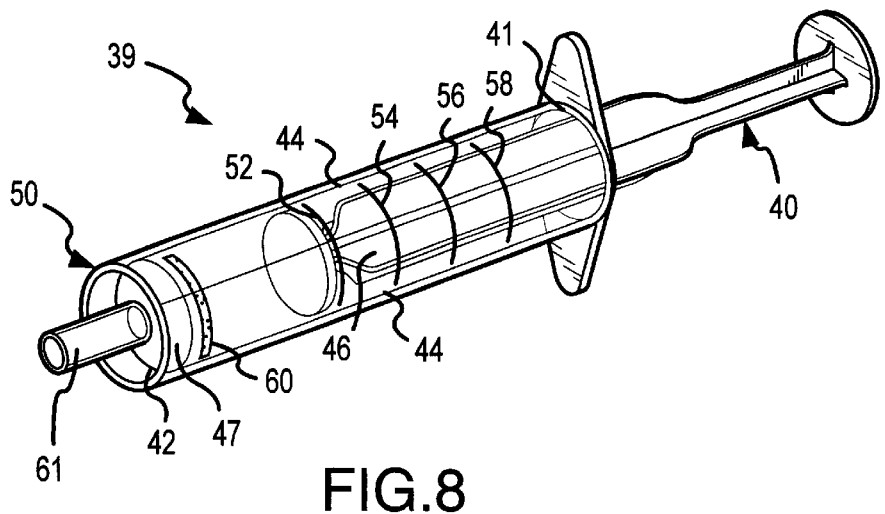
FIG. 8 is a perspective view of the syringe and sleeve shown in FIG. 6, after filling the syringe to a desired volume.

A preferred embodiment of a medicine dose system 39 of the present invention, as shown in FIGS. 6, 7 and 8, includes a medical syringe 40 and substantially transparent sleeve 50. As is also shown in FIG. 4, syringe 40 contains a preferably cylindrical barrel 41, although the barrel may be other alternative shapes (e.g., conical, square, rectangular, etc). Barrel 41 is preferably manufactured from any conventional material, most preferably a transparent plastic. Barrel 41 may be either unmarked as shown or, in the alternative, may contain conventional volumetric markings. Syringe 40 includes a leading wall 42 and side wall or walls 44, depending on the shape of syringe 40. Slidably mounted in barrel 41 of syringe 40 is a plunger 46 having a leading plunger end 47.

Figure 1:
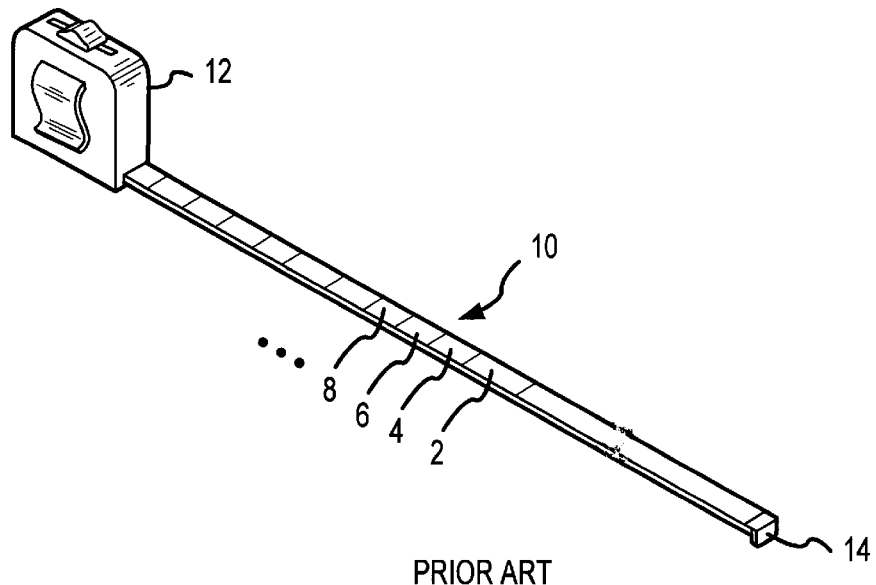
FIG. 1 (prior art) is a perspective view of a measuring tape which correlates a length of a patient with a coded range.
Figure 2:
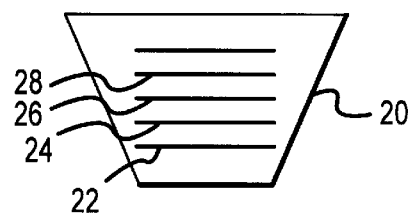
FIG. 2 (prior art) is a side view of a medicine cup which may be used with the measuring tape shown in FIG. 1
Figure 3:
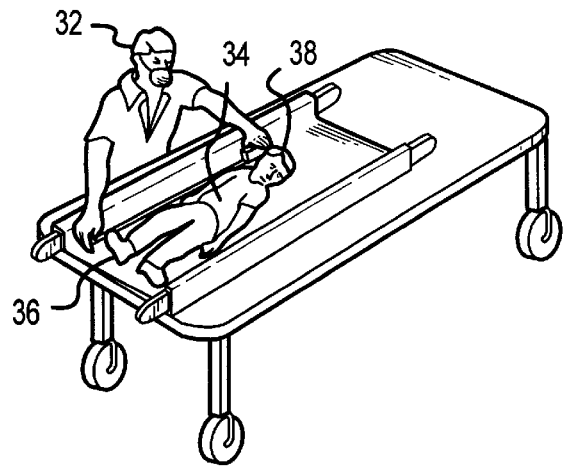
FIG. 3 (prior art) is a perspective view of a physician using the measuring tape shown in FIG. 1 to measure a patient in accordance with the prior art.
Figure 5:
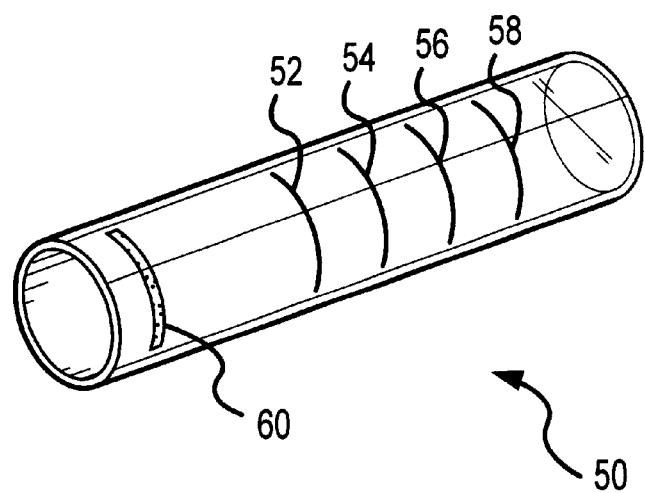
FIG. 5 is a perspective view of a sleeve of the present invention that may be used in conjunction with the syringe shown in FIG. 4.

Referring now to FIG. 5, it can be seen that sleeve 50 of the preferred embodiment of medicine dose system 39 is open at both ends, is cylindrical, and is sized to slide easily onto, fit snugly over and frictionally but releasably engage, barrel 41 of syringe 40. In the most preferred embodiment, sleeve 50 includes a plurality of color coded indicia 52, 54, 56, 58, etc. which correspond to the colors of tape 10 (FIG. 1). By way of example, indicia 52 is a red mark, indicia 54 is a green mark, indicia 56 is a yellow mark, and indicia 58 is a blue mark. Sleeve 50 additionally includes a black indicia 60 that may be distinctly different than the other indicia of system 39, for a purpose further described below.

Figure 11:
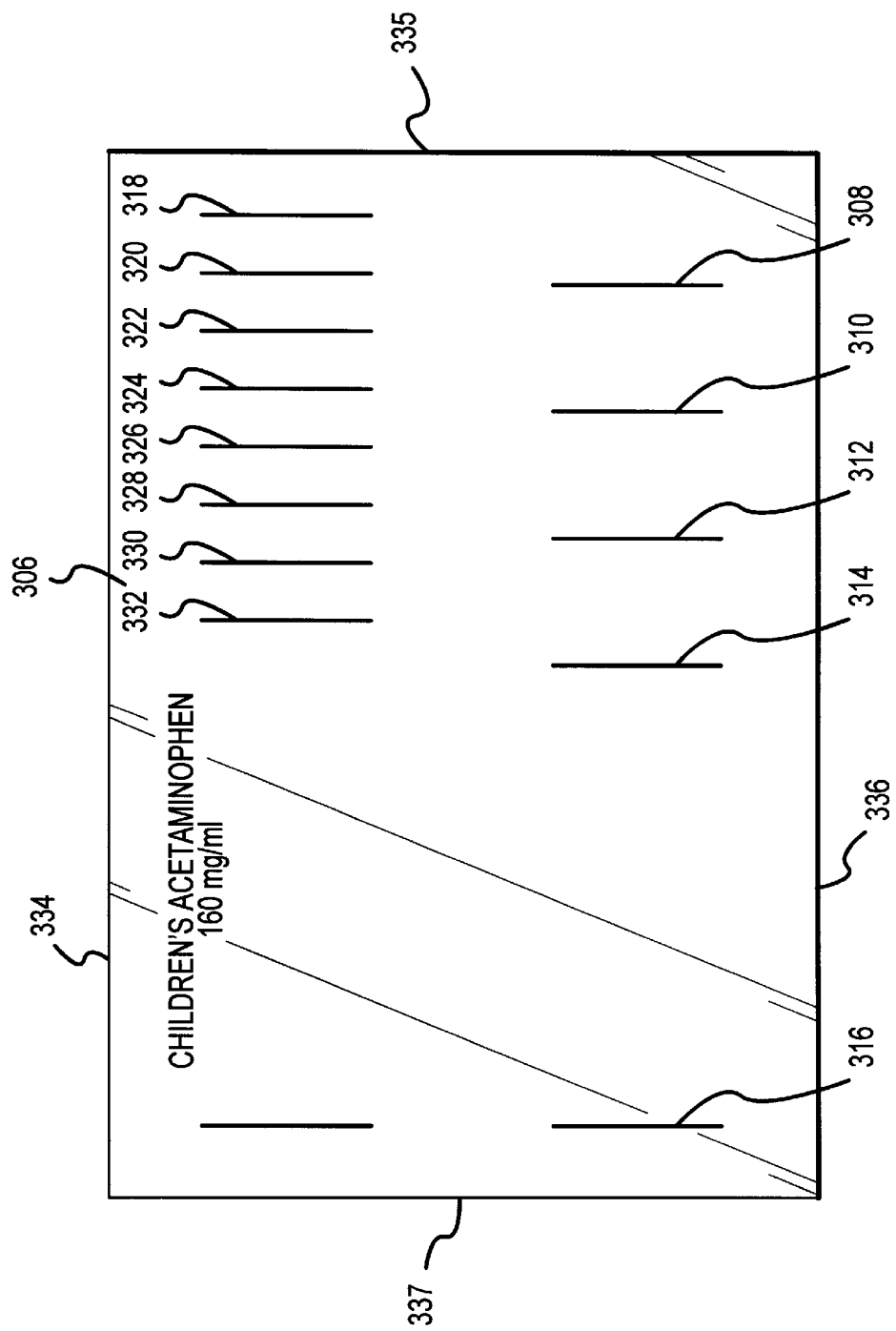
FIG. 11 is a top view of a flat rectangular piece of plastic used in the manufacture of the sleeve of the present invention.

In the preferred embodiment, sleeve 50 is manufactured by imprinting with one or more colors using standard offset printing technology or any equivalent method on a flat rectangle of transparent or translucent plastic (see FIG. 11). When indicia 52, 54, 56 and 58 are parallel lines, consistent registration of indicia 52, 54, 56 and 58 is achieved by imprinting each of the lines of indicia 52, 54, 56 and 58 relative to one parallel edge of the flat rectangle of plastic parallel. After imprinting, sleeve 50 is rolled to form a substantially transparent or translucent cylinder, with opposing parallel sides fixedly attached, with the term "substantially transparent or translucent" used herein to mean a sleeve having at least 33% of its surface area transparent or translucent in a manner sufficient to allow an operator to see the medication fluid level in the syringe.

Referring again to FIGS. 6, 7 and 8, sleeve 50 is shown fitted over syringe 40 while a predetermined dose of medicine corresponding in volume to a dose appropriate for color range indicated by indicia 54 is drawn into barrel 41. Initially, indicia 60 of sleeve 50 is aligned with leading wall 42 of syringe 40. This alignment is preferably maintained while the dose of medicine fills syringe 50. As shown in FIG. 6, prior to receiving the medicine, plunger 46 is pushed forward so that leading plunger end 47 contacts leading wall 42 and indicia 60 is aligned with leading wall 42.

Referring now to FIG. 7, it can be seen that syringe 50 also includes a hollow tip 61 (which may be a needle) which is in fluid contact with the medicine (not shown). Plunger 46 is withdrawn along side wall 44 away from leading wall 42, thereby partially filling barrel 41 of syringe 40 with the medicine.

Assuming it has been determined that the appropriate dose of medication to be dispensed from the syringe corresponds to coded range 4 (green in the above example), plunger 46 is withdrawn until leading end 47 of plunger 46 aligns with green indicia 54 of sleeve 50 (see FIG. 8). In this way, the volume of medicine predetermined to be appropriate for patient 34 is ready for dispensing to patient 34.

Figure 9:
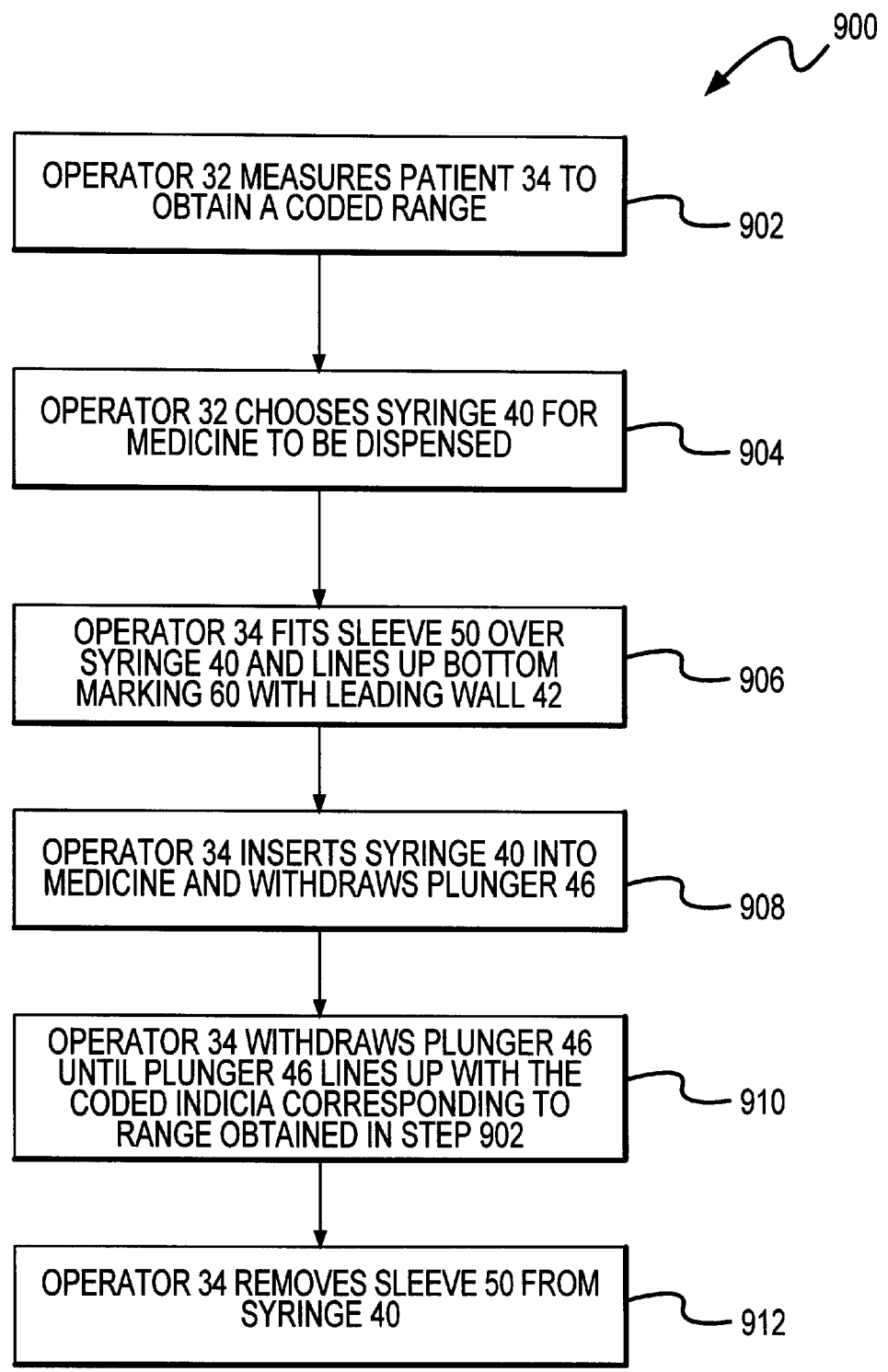
FIG. 9 is a flow diagram showing a method of measuring a dose of medicine in accordance with the present invention.

FIG. 9 is a flow diagram 900 of a preferred method of utilizing the medicine dose dispensing system 39 of the present invention. First, operator 32 measures patient 34 to obtain a coded range, for example, yellow range 6 (Step 902). Next, operator 32 selects syringe 40 as the proper size for the medicine to be dispensed (Step 904). Operator 32 then fits the appropriate sleeve 50 over syringe 40, aligning indicia 60 of sleeve 50 with leading wall 42 of syringe barrel 41 (Step 906). Operator 32 then inserts hollow tip 61 into the medicine and withdraws plunger 46 (Step 908) until leading end 47 of plunger 46 is aligned with yellow indicia 56 of sleeve 50, thereby filling syringe 50 with the correct dose of medicine (Step 910). Prior to dispensing the medicine, it is preferred to remove sleeve 50 from syringe 40, but not necessary (Step 912).

As described above, sleeve 50 slides onto and fits snugly over syringe 40, with sleeve 50 easily removed for reuse with another syringe. It is preferable for sleeve 50 to be removable, so that a particular sized syringe 40 may be used to dispense several different medicines with differing dosage levels. Additionally, it is noted that the inside surface of sleeve 50 could also define structural variations, such as raised bumps or laterally extending ribs, to enhance the frictional engagement between the sleeve and the syringe barrel 41 (not shown).

Figure 10:
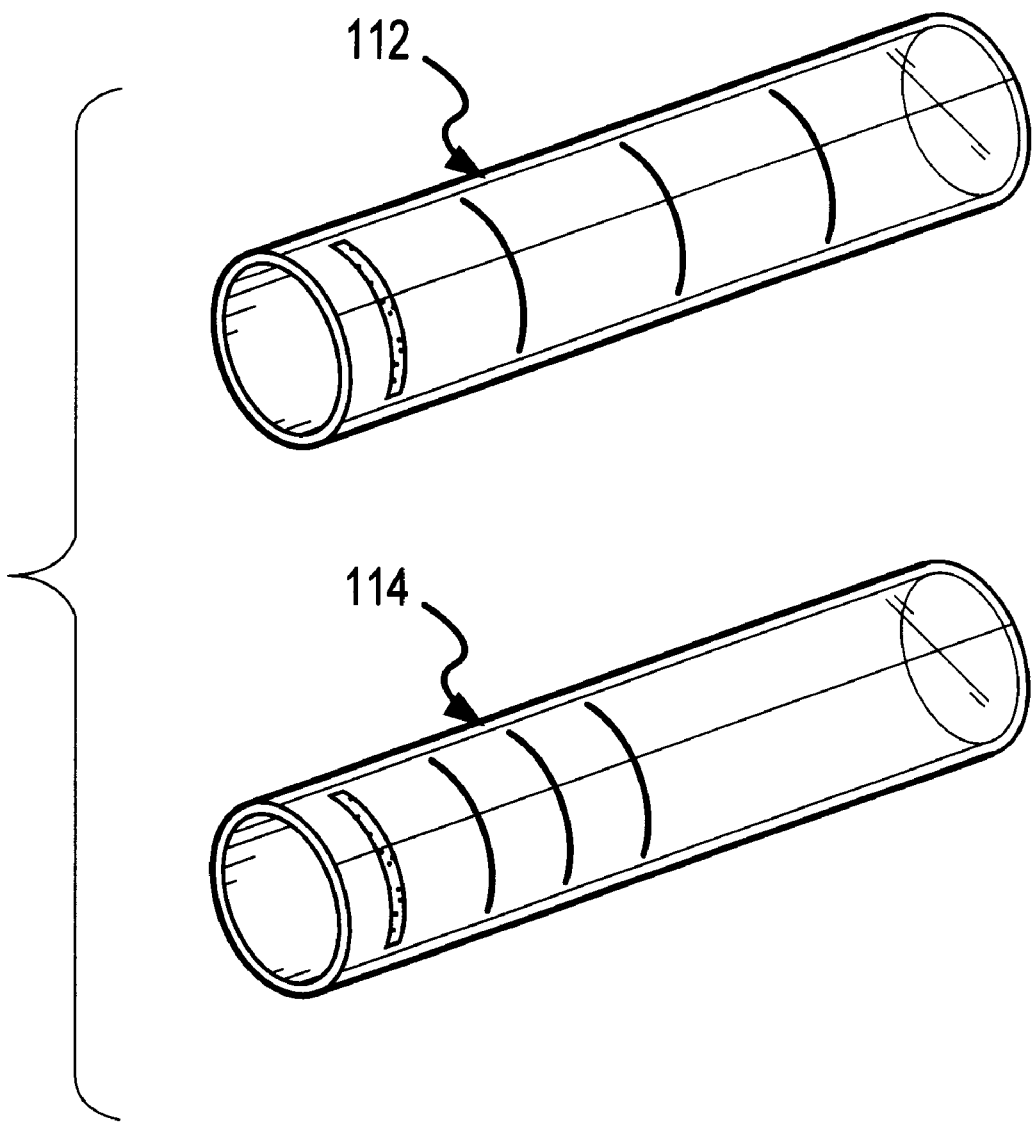
FIG. 10 is a perspective view of a plurality of sleeves for use with a syringe system of the present invention.

Referring now to FIG. 10, other embodiments of the present invention include two sleeves 112 and 114 for measuring dosages of two different medicines in the same sized syringe for a single patient. Depending on which medicine is to be administered, the proper sleeve is fitted to the syringe for use. If the sleeves were permanently attached to syringe 40, or alternatively syringe 40 was itself marked, each medicine would have to have its own syringe for application, which is more expensive than having one syringe and multiple sleeves.

In another embodiment of the present invention (not shown), a sleeve 50 adapted to fit a predetermined sized syringe 40 contains only a single indicia (e.g., a single black line) corresponding to either a predetermined dose of the medicine to be dispensed from syringe 40 or a code which is directly related to a predetermined dose of medicine to be dispensed from syringe 40. This embodiment of the present invention may optionally include a second marking which is an alignment indicia (e.g., a second black mark), which is used to position sleeve 50 on syringe 40.

In still another embodiment of the present invention (not shown), syringe 40 is prefilled with a fixed volume of medicine, and a substantially transparent or translucent sleeve which is tinted with a red, blue, or other colored tint may be permanently mounted around the barrel 41 of syringe 40. The color tint corresponds to a predetermined coded range, given the concentration of the particular medicine. Alternatively, the color-tinted sleeve may be tinted to allow or prevent predetermined wave-lengths of light from reaching the medicine.

FIGS. 11–15 illustrate yet other embodiments of the present invention where re-useable sleeves 300' and 300" are manufactured and packaged to form non-cylindrical elongated tubes. Sleeves 300' and 300" are shaped with the walls of tube 302 defining a substantially trapezoidal, diamond shaped or rectangular passageway 304.

Referring now to FIG. 11, sleeves of the present invention are preferably manufactured from a flat rectangle of plastic 306 (although other materials are envisioned) having opposing parallel sides 334 and 336 and opposing ends 335 and 337. As discussed briefly above, plastic rectangle 306 is preferably imprinted with one or more color indicia 308, 310, 312 and 314 which correspond to dosages for predetermined coded ranges. Rectangle 306 may also include a black indicia 316 (not shown) used to align the finished sleeve with leading wall 42 of syringe 40. Additionally, plastic rectangle 306 may be imprinted with a series of volumetric or drug dose indicia 318, 320, 322, 324, 326, 328, 330 and 332 that specify pre-determined volumes or doses of a specific drug, liquid or suspension for administration to a patient. In addition, rectangle 306 is imprinted with text, for example, "children's acetaminophen suspension 160 mg/ml", describing the concentration of the contents, with indicia 318, 320, 322, 324, 326, 328, 330 and 332 corresponding to 50 mg acetaminophen intervals. After imprinting, plastic rectangle 306 is gripped, with opposing parallel sides 334 and 336 overlapped and fixedly attached with adhesive to form a longitudinal seam (although other attachment means such as heat treatment may be employed), thereby defining a sleeve of the present invention.

Figure 12:
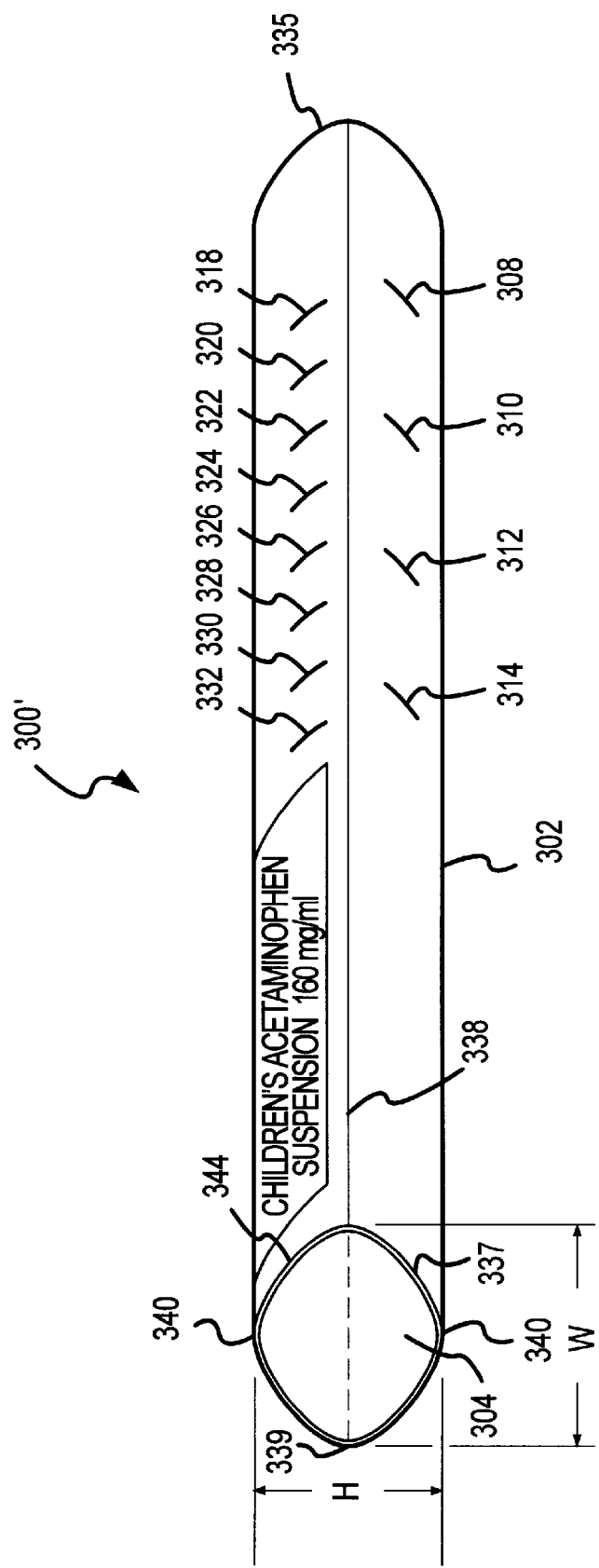
FIG. 12 is a perspective view of a non-cylindrical sleeve of the present invention that may be used in conjunction with the syringe shown in FIG. 4.

Referring now to FIG. 12, in a preferred embodiment sleeve 300' is crimped or pressed in half to create opposing folds 338 and 339. The material from which sleeve 300' is manufactured is sufficiently stiff and also resilient to create a spring-like action about folds 338 and 399 and maintain arcs 340 between opposing folds 338 and 339 without draping therebetween. In this configuration, width "W" of sleeve 300' is wider than height "H" of sleeve 300' and height "H" is slightly smaller than the outside diameter of the barrel of the syringe over which sleeve 300' is to be placed. Accordingly, in order to place sleeve 300' over the syringe barrel, sleeve 300' is grasped at folds 338 and 339 and pinched slightly, thereby increasing height "H" and decreasing width "W" to both closely approximate the outside diameter of the syringe barrel and allow the sleeve 300' to slide onto the barrel. The resilient quality of sleeve 300' and the spring-like character of folds 338 and 339 causes sleeve 300' to grip the syringe barrel and maintain frictional engagement therewith. After drawing medication into the syringe barrel to a desired volume, however, sleeve 300' can be easily removed for subsequent reuse.

Figure 13:
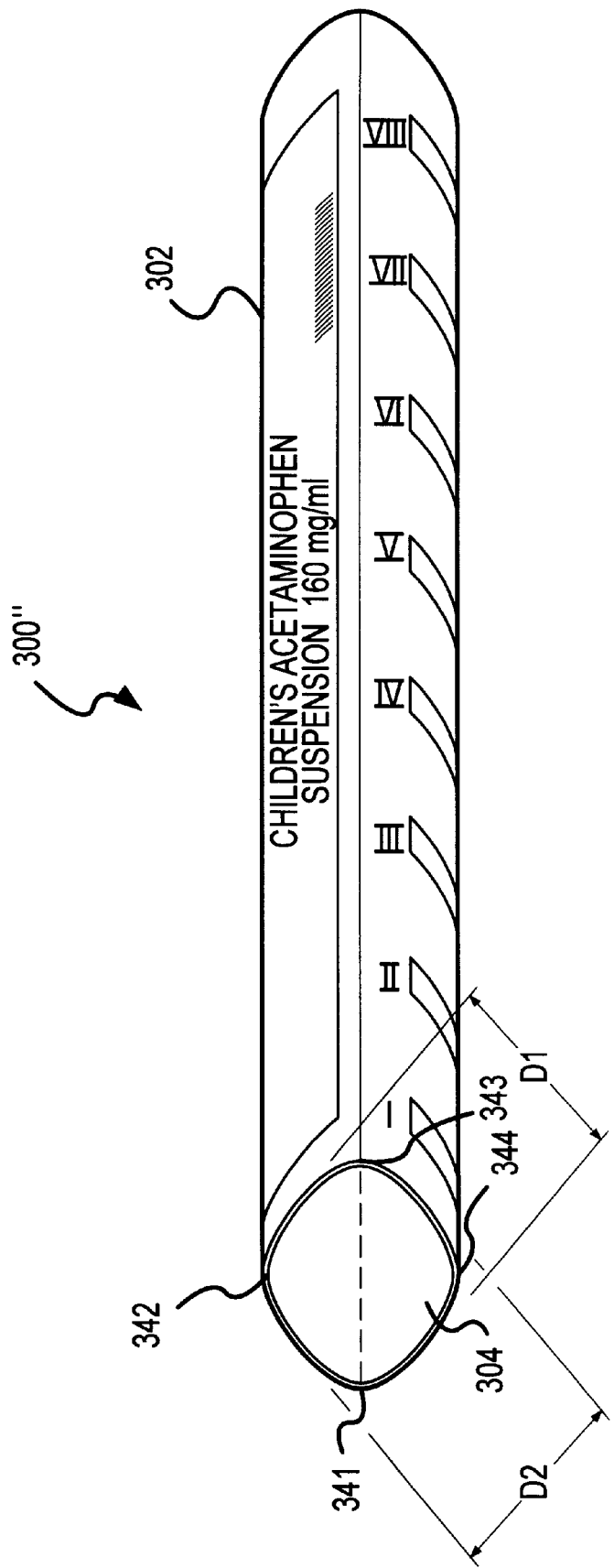
FIG. 13 is a perspective view of another non-cylindrical sleeve of the present invention.

Referring now to FIG. 13, in yet another preferred embodiment, sleeve 300" is crimped to form four folds 341, 342, 343 and 344. In this case, diameters "D1" and "D2" are approximately equal. The material from which sleeve 300" is manufactured is sufficiently stiff and also resilient to maintain arcs 345 between adjacent folds 341, 342, 343 and 344, and not drape therebetween. In this configuration, "D1" and "D2" are both slightly smaller than the outside diameter of the barrel of the syringe over which sleeve 300" is to be placed. Accordingly, in order to place sleeve 300" over the syringe barrel, sleeve 300" is pinched slightly and slid onto the barrel. The resilient quality of sleeve 300" and the spring-like character of folds 341, 342, 343 and 344 cause sleeve 300" to grip the syringe barrel and maintain frictional engagement therewith. After drawing medication into the syringe barrel to a desired volume, however, sleeve 300" can be easily removed for subsequent reuse.

Figure 14:
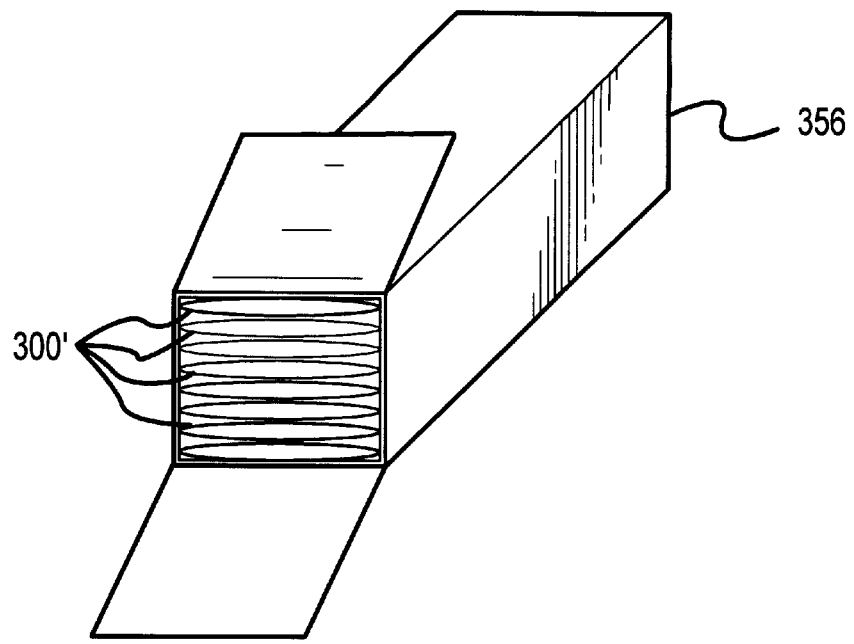
FIG. 14 is a perspective view of a plurality of the sleeves shown in FIG. 12 packaged together.

FIG. 14 illustrates a packaging arrangement for a plurality of if sleeves 300'. Sleeves 300' are packaged overlying each other in a box 356.

Figure 15:
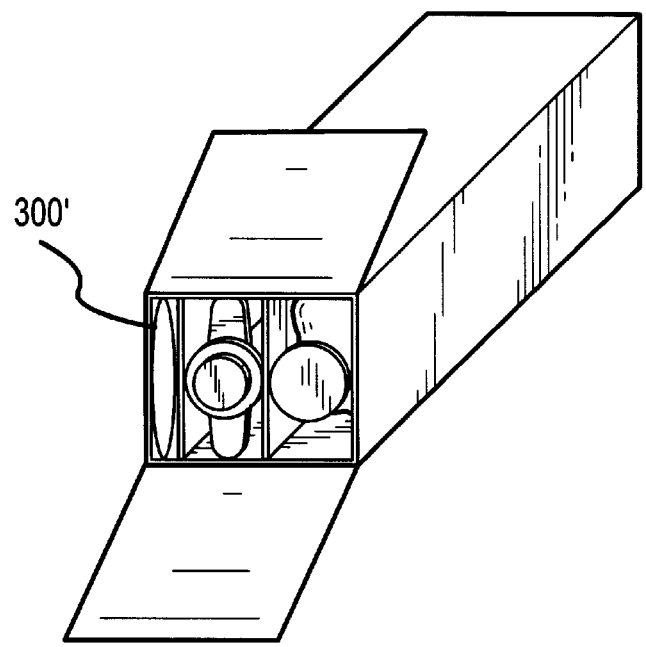
FIG. 15 is a perspective view of the sleeve shown in FIG. 12 packaged with a syringe like that shown in FIG. 4.

FIG. 15 illustrates another packaging arrangement wherein a sleeve 300' is packaged with a correspondingly sized syringe and a container of medication.

Figure 16:
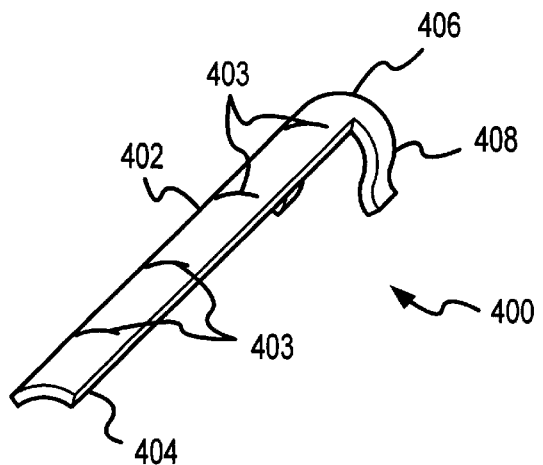
FIG. 16 is a perspective view of another syringe adapter of the present invention used to identify coded ranges for dispensation of medicine from a syringe.
Figure 17:
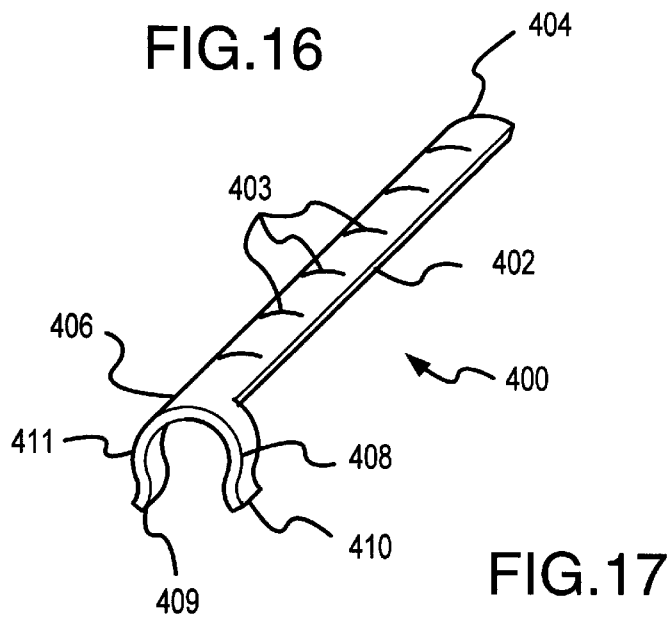
FIG. 17 is another perspective view of the syringe adapter shown in FIG. 16.

FIGS. 16 and 17 illustrates yet another syringe dosage identification technique of the present invention. As shown in FIGS. 16 and 17, a removable and reusable syringe marker 400 includes an elongated strip 402 containing coded indicia 403 thereupon and having a first end 404 and an opposing second end 406. Extending transversely from second end 406 is collar 408 with terminal ends 409 30 and 410. Collar 408 is sized to have an inside diameter slightly smaller than the outer diameter of the syringe barrel to which it is mounted. To use syringe marker 400, terminal ends 409 are spread apart slightly, to allow collar 408 to encircle and grip a barrel of a syringe. Syringe marker 400 is then slid down along the length of the syringe barrel until the leading face 411 of collar 408 abuts the leading face of the finger grips of the syringe. The plunger is then withdrawn in the syringe barrel until adjacent the desired coded indicia 403, as previous described in connection with other embodiments of the present invention.

Figure 18:
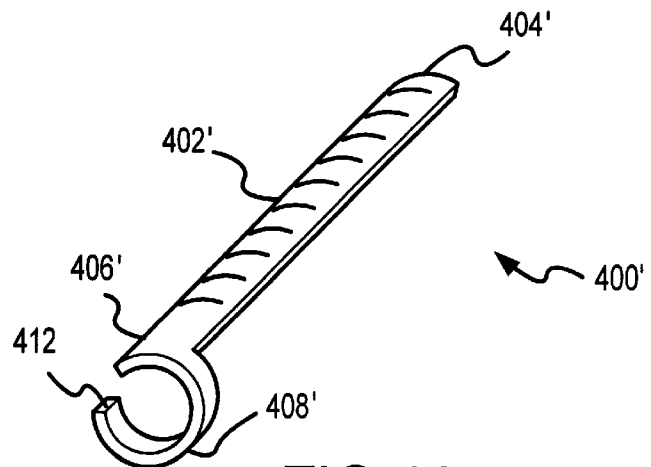
FIG. 18 is a perspective view of another syringe adapter of the present invention used to identify coded ranges for dispensation of medicine from a syringe.

FIG. 18 illustrates another variation of the syringe marker 400 of the present invention. As shown in FIG. 18, a removable and reusable syringe marker 400' includes an elongated strip 402' containing coded indicia 403' thereupon and having a first end 404' and an opposing second end 406'. Extending transversely from second end 406' is collar 408', having but one terminal end 412. Collar 408' is sized to have an inside diameter slightly smaller than the outer diameter of the syringe barrel to which it is mounted. To use syringe marker 400', terminal end 412 is spread apart from second end 406' of marker 400' to allow collar 408' to encircle and grip a syringe barrel. Further use of marker 400' is similar to that described above in connection with marker 400.

Although collars 408 and 408' are described above in connection with markers 400 and 400', respectively, for removable and reusable engagement with a syringe, other methods of temporary attachment of syringe marking systems are contemplated. For example, strips 402 may be temporarily attached to syringes with interlocking tabs and pockets, hook and eye systems such as the Velcro™ materials, clips and temporary adhesives.

Figure 19:
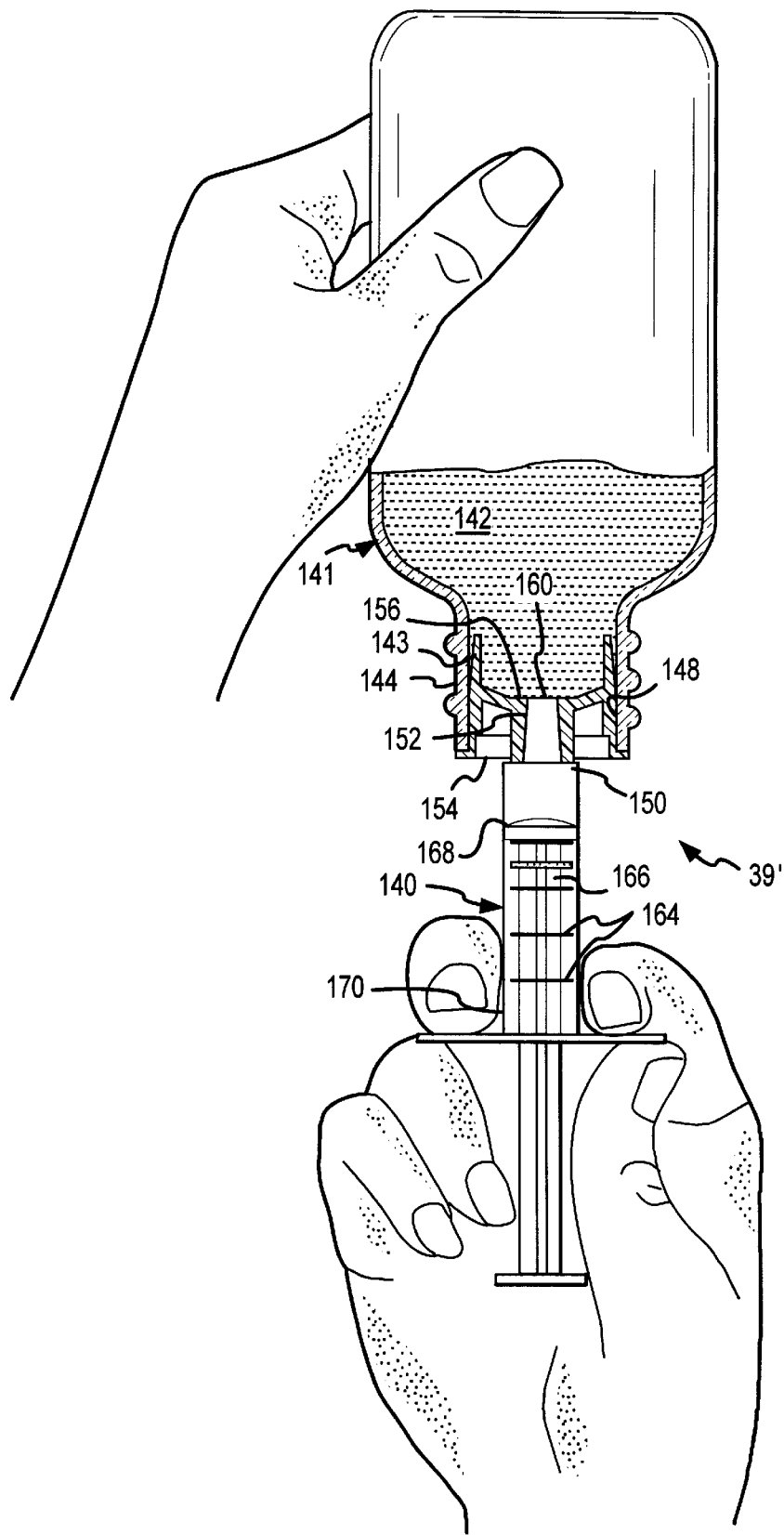
FIG. 19 is a side elevation view of another alternative embodiment of the medicine dose system of the present invention.

FIG. 19 illustrates another embodiment of the medicine dose system of the present invention. Medicine dose system 39' includes a syringe 140, a substantially transparent or translucent sleeve 150, a container 141 containing medication 142 to be dispensed, and an adapter 143 positioned in the neck 144 of container 141. (Containers and adapters like those described herein are described in more detail in U.S. Pat. Nos. 4,317,448 and 4,303,071 both entitled SYRINGE-TYPE LIQUID CONTAINER DISPENSER ADAPTER, both of which are assigned to the Assignee of this application, and both of which are incorporated by this reference herein.) Adapter 143 has at least two circumferential flanges 145 for frictional and sealing engagement with inner wall 148 of neck 144 of container 141. Centrally formed in adapter 143 is a passageway 152 extending from the exposed face 154 of adapter 143 to the interior face 156 thereof. The outer portion 158 of passageway 152 which is adjacent exposed face 152 is shaped to receive the hollow tip 160 of syringe 140. Most typically, outer portion 158 of passageway 152 is substantially conical, although other shapes and volumes are contemplated, provided outer portion 158 conforms to and receives tip 160. Inner portion 162 of passageway 152 may also be conical, although it preferably has a diameter at its widest point which is substantially greater than the diameter of outer portion 158 adjacent exposed face 154. As described above in connection with the various embodiments of the present invention, sleeve 150 includes one or more indicia 164 representative of coded ranges previously correlated to particular volumes of the medication with which syringe 140 is to be filled for administration to a particular patient.

A preferred method of filling syringe 140 utilizing medicine dose system 39' initially involves the identification of the coded range to associated with the patient to be treated by the techniques previously described. The proper sleeve 150 and syringe 140 are then selected, given the medicine to be administered, and sleeve 150 is positioned on syringe 140. Container 141 of the desired medicine is grasped in one hand, and syringe 140 with sleeve 150 is grasped in the other hand. Tip 160 of syringe 140 is then inserted into outer portion 158 of passageway 152 of adapter 143, until flush therein. Container 141 and syringe 140 are then inverted, with tip 160 of syringe 140 maintained in a flush position in outer portion 158 of passageway 152 but pointing upward. Medicine flows and fills inner portion 162 in this inverted position. Plunger 166 of syringe 140 is then retracted until the leading plunger end 168 is adjacent the desired indicia 164. If air is present in the barrel 170 or tip 160 of syringe 150 adjacent the medicine, then plunger 166 is partially or fully depressed, until the air is ejected out tip 160 and into container 141, after which plunger 166 is then retracted again, until leading plunger end 168 is once again adjacent the desired indicia 164. Syringe 140 is then disengaged from contact with container 141 and the medicine dispensed to the patient, with or without removal of sleeve 150.

Figure 20:
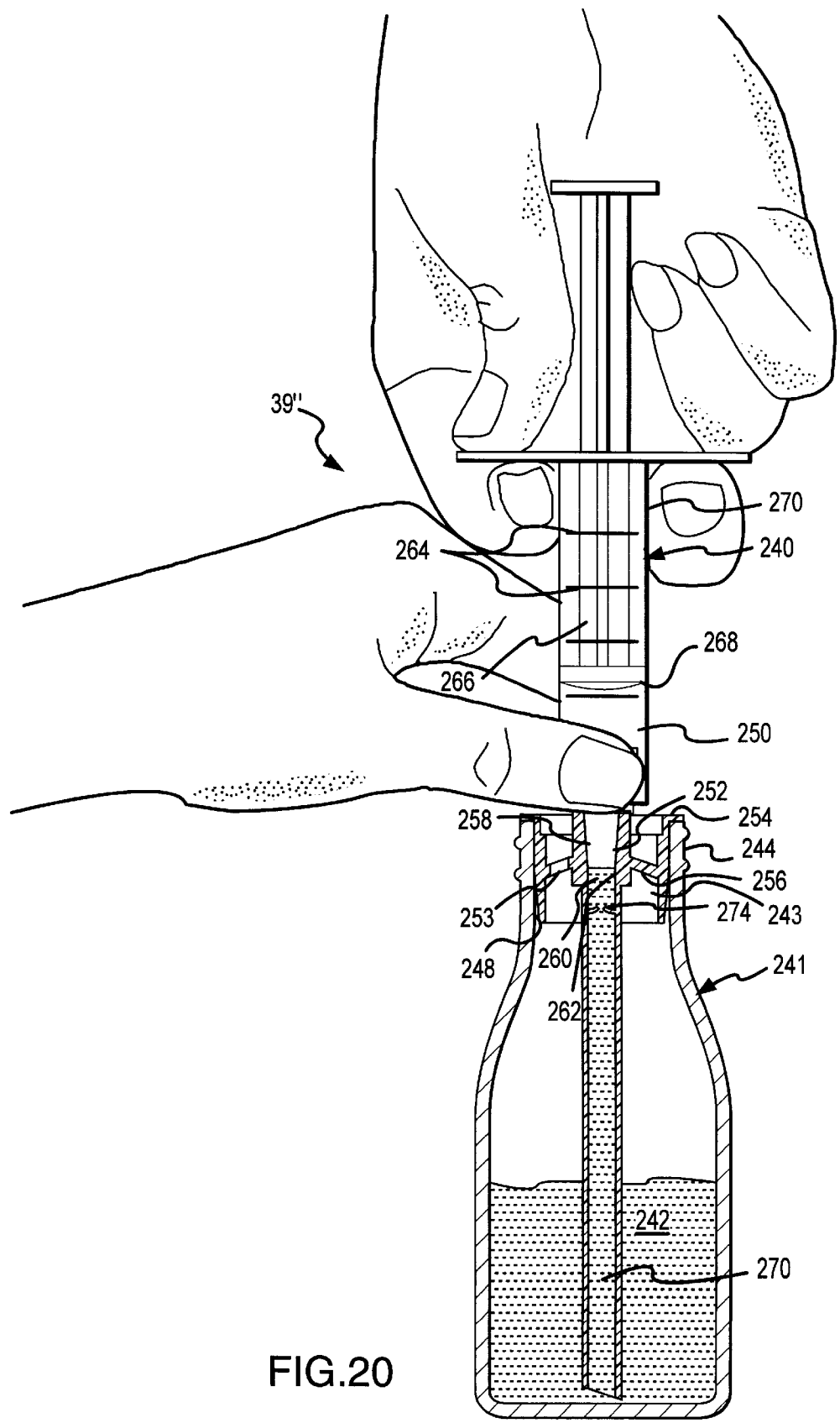
FIG. 20 is a perspective view of another removable and reusable coded range indicia identifier of the present invention.

FIG. 20 illustrates yet another embodiment of the medicine dose system of the present invention. Medicine dose system 39" includes a syringe 240, a substantially transparent or translucent sleeve 250, a container 241 containing medication 242 to be dispensed, and an adapter 243 positioned in the neck 244 of container 241. Adapter 243 has at least two flanges 245 for frictional and sealing engagement with inner wall 248 of neck 244 of container 241. Centrally formed in adapter 243 is a first passageway 252 and a second passageway 253, which extend from the exposed face 254 of adapter 43 to the interior face 256 thereof. The outer portion 258 of first passageway 252 which is adjacent exposed face 254 is shaped to receive the hollow tip 260 of syringe 240. Most typically, outer portion 258 of first passageway 252 is substantially conical, although other shapes and volumes are contemplated, provided outer portion 258 conforms to and receives tip 260. In fluid communication with the inner portion 262 of first passageway 252 and operatively coupled to adapter 243 is a tube 270, which extends downward through medicine 242 contained therein. Formed in adapter 243 adjacent the inner portion 262 of first passageway 252 is a valve 274, which may be a centrally formed diaphragm with a slit thereacross. As described above in connection with the embodiments of the present invention, sleeve 250 includes one or more indicia 264 representative of coded ranges previously correlated to particular volumes of the medication to which syringe 240 is to be filled for administration to particular patients.

A preferred method of filling syringe 240 utilizing medicine dose system 39" initially involves the identification of a desired coded range by the techniques described above. The proper sleeve 250 and syringe 240 are selected, given the medicine to be administered, and sleeve 250 is positioned on syringe 240. While container 241 is in an upright position, syringe 240 with sleeve 250 is positioned over container 241, with tip 260 of syringe 240 inserted into outer portion 258 of passageway 252, until flush therein. Plunger 266 of syringe 240 is retracted until the leading plunger end 268 is adjacent selected indicia 264. Medicine 272 is thereby drawn up through tube 270 past one-way valve 274, filling syringe tip 260 and barrel 270. If air is present in the barrel 270 or tip 260 of syringe 250 adjacent the medicine, then syringe 250 is removed from first passageway 252, tip 260 is pointed upward, plunger 266 is partially or fully depressed, until the air is ejected out tip 260. Tip 260 is then placed again in outer portion 258 of first passageway 252, plunger 266 is retracted again until leading plunger end 268 is once again adjacent the desired indicia 264. Syringe 240 is then disengaged from contact with container 241 and the medicine dispensed to the patient, with our without removal of sleeve 250.

Reference has been made in detail to presently preferred embodiments of the invention, examples of which are illustrated in the accompanying drawings. It is intended that all matter contained in the description above or shown in the accompanying drawings shall be interpreted as illustrative and not in a limiting sense. Moreover, other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A system for dispensing a dose of medication to a patient from a syringe, wherein the dose is based on a predetermined patient value that corresponds to a coded range, the system comprising:
    a syringe having a barrel adapted for receiving the medication and a plunger adapted for drawing the medication into the barrel and dispensing the medication therefrom; and
    a resilient sleeve adapted for removably encircling the barrel of the syringe and for re-use, wherein the sleeve contains indicia corresponding to at least one coded range.

2. The system of claim 1 wherein the indicia includes a plurality of colored marks each associated with a coded range.

3. The system of claim 2 wherein the plurality of colored marks indicates lengths of the syringe barrel to which the plunger is drawn to fill the barrel with a predetermined amount of the medication to be received.

4. The system of claim 3 wherein the sleeve is slidably and releasably positioned on said barrel, for releasable and frictional engagement with said barrel.

5. The system of claim 3 wherein the sleeve contains at least two folds along the longitudinal axis of the sleeve.

6. The system of claim 2 wherein the sleeve further contains alignment indicia to align the sleeve on the barrel.

7. The system of claim 2 wherein the sleeve contains at least two folds along the longitudinal axis of the sleeve.

8. The system of claim 2 wherein the syringe further includes a tip and the system further comprises:
    a container having a neck and containing the medication to be drawn in the barrel of the syringe and dispensed from the syringe; and
    an adapter positioned in the neck of the container having a passageway formed therein for receiving the syringe tip in conforming engagement therewith.

9. The system of claim 2 wherein the syringe further includes a tip and the system further comprises:
    a container having a neck and containing the medication to be drawn in the barrel of the syringe and dispensed from the syringe;
    an adapter positioned in the neck of the container having a passageway formed therein for receiving the syringe tip, a tube operatively coupled to the adapter and extending therefrom into the container, and a valve mounted centrally therein, wherein upon receipt of the syringe tip in the passageway of the adapter and withdrawal of the plunger in the barrel of the syringe, the system is operative to withdraw medication in the container up through the tube, past the syringe tip and into the barrel of the syringe, and when the syringe containing medicine and the syringe tip is removed from the passageway of the adapter, the valve is operative to maintain medication in the tube.

10. The system of claim 1 wherein the sleeve is slidably and releasably positioned on said barrel, for releasable and frictional engagement with said barrel.

11. The system of claim 10 wherein the syringe further includes a tip and the system further comprises:
    a container having a neck and containing the medication to be drawn in the barrel of the syringe and dispensed from the syringe; and
    an adapter positioned in the neck of the container having a passageway formed therein for receiving the syringe tip in conforming engagement therewith.

12. The system of claim 10 wherein the syringe further includes a tip and the system further comprises:
    a container having a neck and containing the medication to be drawn in the barrel of the syringe and dispensed from the syringe;
    an adapter positioned in the neck of the container having a passageway formed therein for receiving the syringe tip, a tube operatively coupled to the adapter and extending therefrom into the container, and a valve mounted centrally therein, wherein upon receipt of the syringe tip in the passageway of the adapter and withdrawal of the plunger in the barrel of the syringe, the system is operative to withdraw medication in the container up through the tube, past the syringe tip and into the barrel of the syringe, and when the syringe containing medicine and the syringe tip is removed from the passageway of the adapter, the valve is operative to maintain medication in the tube.

13. The system of claim 1 wherein the sleeve contains at least two folds along the longitudinal axis of the sleeve.

14. The system of claim 13 wherein the syringe further includes a tip and the system further comprises:
    a container having a neck and containing the medication to be drawn in the barrel of the syringe and dispensed from the syringe; and
    an adapter positioned in the neck of the container having a passageway formed therein for receiving the syringe tip in conforming engagement therewith.

15. The system of claim 13 wherein the syringe further includes a tip and the system further comprises:
    a container having a neck and containing the medication to be drawn in the barrel of the syringe and dispensed from the syringe;
    an adapter positioned in the neck of the container having a passageway formed therein for receiving the syringe tip, a tube operatively coupled to the adapter and extending therefrom into the container, and a valve mounted centrally therein, wherein upon receipt of the syringe tip in the passageway of the adapter and withdrawal of the plunger in the barrel of the syringe, the system is operative to withdraw medication in the container up through the tube, past the syringe tip and into the barrel of the syringe, and when the syringe containing medicine and the syringe tip is removed from the passageway of the adapter, the valve is operative to maintain medication in the tube.

16. The system of claim 1 wherein the syringe further includes a tip and the system further comprises:
- a container having a neck and containing the medication to be drawn in the barrel of the syringe and dispensed from the syringe; and
- an adapter positioned in the neck of the container having a passageway formed therein for receiving the syringe tip in conforming engagement therewith.

17. The system of claim 1 wherein the syringe further includes a tip and the system further comprises:
- a container having a neck and containing the medication to be drawn in the barrel of the syringe and dispensed from the syringe;
- an adapter positioned in the neck of the container having a passageway formed therein for receiving the syringe tip, a tube operatively coupled to the adapter and extending therefrom into the container, and a valve mounted centrally therein, wherein upon receipt of the syringe tip in the passageway of the adapter and withdrawal of the plunger in the barrel of the syringe, the system is operative to withdraw medication in the container up through the tube, past the syringe tip and into the barrel of the syringe, and when the syringe containing medicine and the syringe tip is removed from the passageway of the adapter, the valve is operative to maintain medication in the tube.

18. An apparatus for dispensing a dose of medication to a patient from a syringe, wherein the dose is based on predetermined value of the patient that corresponds to a coded range, and the syringe includes a barrel adapted for receiving the medication and a plunger adapted for drawing the medication into the barrel and dispensing the medication from the syringe, said apparatus comprising:
- a resilient sleeve adapted for removably and reusably encircling the barrel of the syringe, wherein the sleeve contains at least one mark corresponding to a coded range.

19. The apparatus according to claim 18, wherein the sleeve contains a plurality of colored marks corresponding to a plurality of the coded ranges.

20. An apparatus for dispensing a dose of medication to a patient from a syringe, wherein the dose is based on predetermined value of the patient that corresponds to a coded range, and the syringe includes a barrel adapted for receiving the medication and a plunger adapted for drawing the medication into the barrel and dispensing the medication from the syringe, said apparatus comprising:
- a removable and reusable elongated marker having means for temporary attachment to said syringe in alignment with the longitudinal axis of the barrel of the syringe, wherein the elongated marker contains a plurality of colored marks corresponding to a plurality of the coded ranges.

21. An apparatus for dispensing a dose of medication to a patient from a syringe, wherein the dose is based on a value of the patient that corresponds to coded ranges, and the syringe includes a barrel adapted for receiving the medication and a plunger adapted for drawing the medication into the barrel and dispensing the medication from the syringe, said apparatus comprising:
- a substantially transparent or translucent sleeve adapted for encircling the barrel of the syringe, wherein the sleeve is color tinted to correspond to a coded range.

22. A system for dispensing a dose of medication to a patient from a syringe, wherein the dose is based on a predetermined patient value that corresponds to a coded range, the system comprising:
- a syringe having a barrel adapted for receiving the medication and a plunger adapted for drawing the medication into the barrel and dispensing the medication therefrom; and
- a substantially transparent or translucent sleeve adapted for removably encircling the barrel of the syringe and for re-use, wherein the sleeve contains indicia corresponding to at least one coded range.

23. The system for dispensing a dose of medication according to claim 22, wherein the indicia include a plurality of colored marks corresponding to a plurality of coded ranges.

24. The system for dispensing a dose of medication according to claim 22, wherein the indicia further comprises the name and concentration of the medication in the syringe.

\* \* \* \* \*